United States Patent [19]

Sontag

[11] Patent Number: 4,654,880
[45] Date of Patent: Mar. 31, 1987

[54] SIGNAL TRANSMISSION SYSTEM
[75] Inventor: Hugh D. Sontag, Maplewood, Minn.
[73] Assignee: Minnesota Mining and Manufacturing Company, St. Paul, Minn.
[21] Appl. No.: 880,357
[22] Filed: Jun. 26, 1986

Related U.S. Application Data

[63] Continuation of Ser. No. 559,923, Dec. 9, 1983, abandoned.
[51] Int. Cl.⁴ .................. H04B 5/00; H04R 25/00
[52] U.S. Cl. .................. 455/41; 455/121; 128/420.6
[58] Field of Search .................. 455/41, 129, 121; 179/82, 107 E; 128/419 PT, 903; 333/108 A

[56] References Cited

U.S. PATENT DOCUMENTS

| | | | |
|---|---|---|---|
| 3,355,667 | 11/1967 | Bevene | 455/129 |
| 3,500,416 | 6/1966 | Ellsworth | 455/41 |
| 3,569,968 | 3/1971 | Love | 455/41 |
| 3,656,132 | 4/1972 | Brumbelow | 455/41 |
| 3,806,831 | 4/1972 | Kleinberg | 331/108 A |
| 4,357,497 | 11/1982 | Hochmair et al. | 179/107 E |
| 4,441,210 | 4/1984 | Hochmair et al. | 455/41 |

Primary Examiner—Robert L. Griffin
Assistant Examiner—Curtis Kuntz
Attorney, Agent, or Firm—Donald M. Sell; James A. Smith; William D. Bauer

[57] ABSTRACT

A signal transmission system for transmitting a signal across a barrier. A radio frequency receiver as coupled to a receiving resonant antenna. A transmitting resonant antenna coupled to a radio frequency transmitter on the other side of the barrier. The resonant frequency of the receiving resonant antenna is relatively close to the resonant frequency of the transmitting resonant antenna. The radio frequency transmitter has an oscillator having a frequency of oscillation driving a resonant load which includes the transmitting resonant antenna and its inductive coupling with the receiving resonant antenna. The frequency of oscillation of the oscillator of the radio frequency transmitter being at least partially determined by the resonant frequency of the resonant load which it drives.

11 Claims, 5 Drawing Figures

SIGNAL TRANSMISSION SYSTEM

This is a continuation of application Ser. No. 559,923, filed Dec. 9, 1983, now abandoned.

TECHNICAL FIELD

The present invention relates generally to signal transmission systems and more particularly to signal transmission systems which transmit a signal across a boundary with close proximity between transmitting and receiving antennas.

BACKGROUND OF THE INVENTION

The environment where the signal transmission system of the present invention operates is in a system where the transmission is over a short distance across a barrier. An example of this environment is the use of a signal transmission system with a hearing prosthetic device in which a receiver is implanted within the body to drive an electrode to electrically stimulate the auditory nerve. A transmitting antenna is positioned in close proximity to the receiving antenna but across the cutaneous barrier. Signals representing sound are then transmitted across the cutaneous boundary to the receiver for ultimate delivery to the electrode. The signal transmission system then avoids the use of a percutaneous plug and its attendant potential for infection.

Typically, the transmitter and receiver of the signal transmission system use resonant LC antennas to transmit and receive a small amount of electrical energy over a short distance, e.g. centimeters over the skin boundary.

Signal transmission systems are in use in which the transmitter utilizes a separate oscillator and antenna. In this situation, the resonant frequencies of each are separate and adjustable. The frequency of the oscillator is adjusted to the unloaded resonant frequency of the antenna. The spacing between the transmitter and receiver is then carefully adjusted to be the distance at which "critical coupling" occurs. The "critical coupling" phenomenon is well known in the art. At the point of "critical coupling" a minimum rate of change of the output level of the receiver with respect to variations in the antenna to antenna spacing is observed. Near "critical coupling" and over a small spacing variation, the output of the receiver is relatively invariant.

However, if larger variations in spacing occur between the transmitting antenna and the receiving antenna, the signal transmitted to the receiver will be diminished.

Similarly, if mismatches are evident between the frequency of oscillation and the resonant frequency of its antenna, the signal transmitted to the receiver will be diminished.

SUMMARY OF THE INVENTION

The present invention provides a signal transmission system for use in transmitting a signal across a barrier. A radio frequency receiver is utilized on one side of the barrier. A receiving resonant antenna is positioned on that one side of the barrier and is operatively coupled to the radio frequency receiver. The receiving resonant antenna has a resonant frequency. A transmitting resonant antenna is positioned on the opposite side of the barrier nearby the receiving resonant antenna. The transmitting resonant antenna has a resonant frequency. The resonant frequency of the receiving resonant antenna is relatively close to the resonant frequency of the transmitting resonant antenna. A radio frequency transmitter is positioned on the same side of the barrier as the transmitting resonant antenna and is operatively coupled to the transmitting resonant antenna. The radio frequency transmitter has an oscillator having a frequency of oscillation driving a resonant load. The resonant load includes the transmitting resonant antenna inductively coupled with the receiving resonant antenna. The frequency of oscillation of the oscillator is at least partially determined by the resonant frequency of the resonant load. In this manner, the transfer characteristic of the signal transmission system is relatively independent of the distance between the transmitting resonant antenna and the receiving resonant antenna, of radial misalignment between the transmitting resonant antenna and of the receiving resonant antenna and resonant frequency mismatch of the transmitting resonant antenna and the receiving resonant antenna.

In a preferred embodiment, the signal transmission system is adapted for use in a transcutaneous environment wherein the receiving resonant antenna and radio frequency receiver are positioned for subcutaneous use and the transmitting resonant antenna and the radio frequency transmitter are positioned for supercutaneous use.

A signal transmission system constructed in this manner provides a transmitter which is self-resonant, i.e. which oscillates at the resonant frequency of the resonant load which includes the transmitting and receiving antennas. This results in the signal level at the receiver being virtually constant over a much wider range of distance variations between the transmitting antenna and the receiving antenna, both axially and laterally. The reason this stability in signal level from the receiver is achieved is due to the effect of the receiving antenna on the resonant frequency of the transmitting antenna coupled with the dependence of the frequency of oscillation of the transmitter on the resonance of the resonant load. This effect causes the operating frequency of the signal transmission system to change such that the output voltage from the receiver stays virtually constant.

BRIEF DESCRIPTION OF THE DRAWINGS

The foregoing advantages, construction and operation of the signal transmission system of the present invention will become more readily apparent from the following description and accompanying drawings in which.

DETAILED DESCRIPTION OF THE PREFERRED EMBODIMENTS

Figure 1:
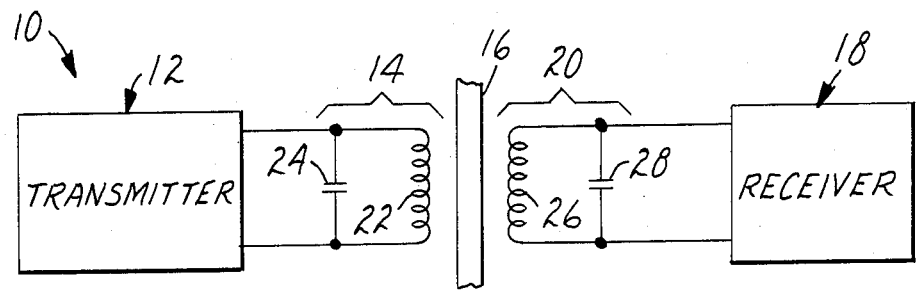
FIG. 1 is a block diagram of a signal transmission system of the present invention.

FIG. 1 illustrates a block diagram of the signal transmission system 10 of the present invention. A transmitter 12 is operatively coupled to a transmitting antenna 14 positioned on one side of a boundary or barrier 16. On the opposite side of the barrier or boundary 16 a receiver 18 is operatively coupled to a receiving antenna 20. In a preferred embodiment, the transmitting antenna consists of a resonant LC circuit involving inductor 22 and capacitor 24. Similarly, in a preferred embodiment, receiving antenna 20 also comprises an LC circuit consisting of inductor 26 and capacitor 28. While both the transmitting antenna 14 and the receiving antenna 20 are shown as tank circuits having a parallel connection of an inductor (22, 26) and a capacitor (24, 28, respectively) various other combinations of capacitive and inductive elements can be formed to comprise a resonant circuit such as, and including, the series combination of an inductor and a capacitor.

The receiving resonant antenna 20 has a resonant frequency which is dependent upon the tank circuit comprising inductor 26 and capacitor 28. Similarly, transmitting antenna 14, in the absence of other factors, has a resonant frequency which is dependent upon the tank circuit comprising inductor 22 and capacitor 24. Inductor 22 of the transmitting resonant antenna 14 and inductor 26 of the receiving resonant antenna 20 are positioned for relatively close lateral alignment along barrier 16 and are also positioned within fairly close proximity across barrier 16, i.e. axial alignment. In a preferred embodiment, the axial spacing between the transmitting antenna 14 and the receiving antenna 20 is chosen such that axial spacing is less than the critical coupling distance. The resonant frequency of the transmitting antenna 14 is chosen so that it is relatively close to the resonant frequency of the receiving antenna 20. Relatively close, for purposes of this discussion, generally means in the range of being within ten percent. Certainly variations in the resonant frequencies of transmitting antenna 14 and receiving antenna 20 can be twenty percent and even greater. However, it is generally preferred that the resonant frequencies of the transmitting antenna 14 and the receiving antenna 20 be within ten percent of each other. Transmitter 12 has an oscillator which drives a resonant load which includes transmitting antenna 14 and its inductive coupling with receiving antenna 20. Further, the frequency of oscillation of the oscillator of transmitter 12 is at least partially determined by the frequency of the resonant load, i.e. the combination of the resonant frequency of transmitting antenna 14 along with the effects of the close proximity of receiving antenna 20. In a preferred embodiment, the frequency of oscillation of the oscillator of transmitter 12 is primarily determined by the resonance of the resonant load and in a still preferred embodiment, is identical to the resonant frequency of the resonant load.

Figure 2:
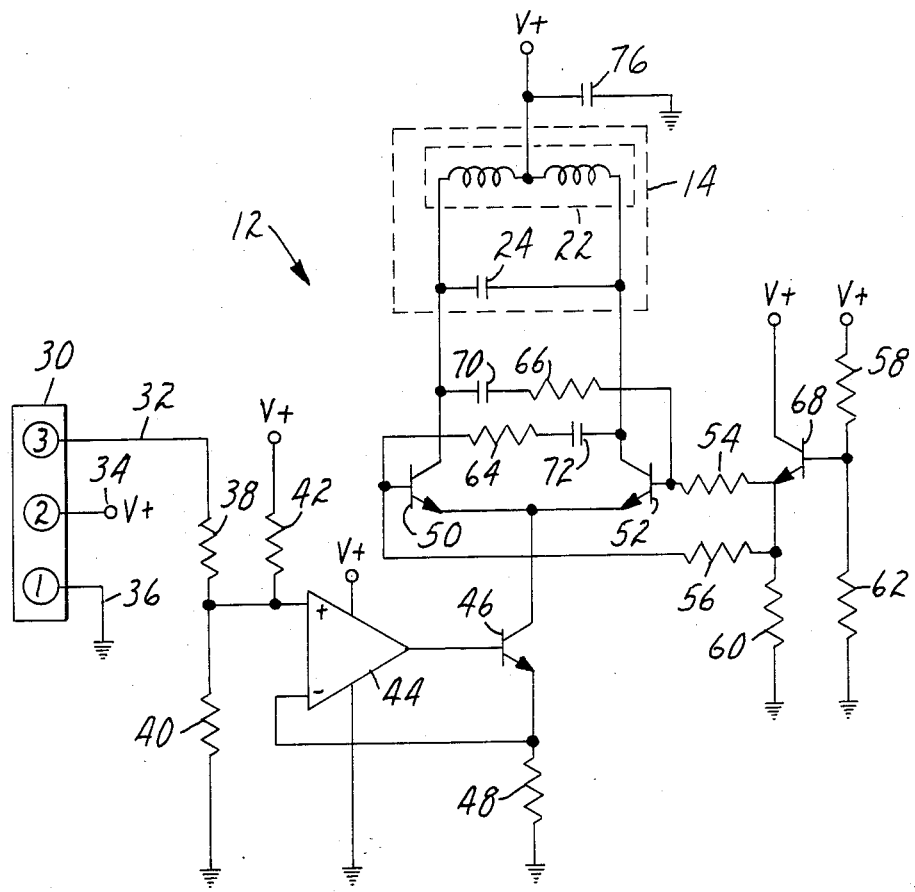
FIG. 2 is a schematic diagram of the transmitter and transmitting antenna.

FIG. 2 illustrates a schematic diagram of the transmitter 12 in conjunction with the transmitting antenna 14. Transmitting antenna 14 consists of a tank circuit comprising inductor 22 and capacitor 24 as illustrated in FIG. 1. The signal to the transmitter 12 is provided through junction block 30 which provides a signal 32, a voltage source 34 and the ground return for the voltage source 36. The signal 32 drives resistor 38, resistor 40, resistor 42, operational amplifier 44 to feed transistor 46 and resistor 48 forms a constant current source, controlled by signal 32. Transistor 46 of the constant current source feeds transistors 50 and 52 which together with associated resistors 54, 56, 58, 60, 62, 64 and 66, transistor 68 and capacitor 70 and 72 form the oscillator circuit of the transmitter 12. This oscillator drives antenna 14 (in the form of inductor 22 along with capacitor 24) to form, in the absence of other circumstances, the resonant load of the oscillator of the transmitter 12. Capacitor 76 is a decoupling capacitor. A distinguishing feature of transmitter 12 is that it contains one oscillator whose frequency of oscillation of that oscillator is dependent upon the resonant load which that oscillator drives.

Figure 3:
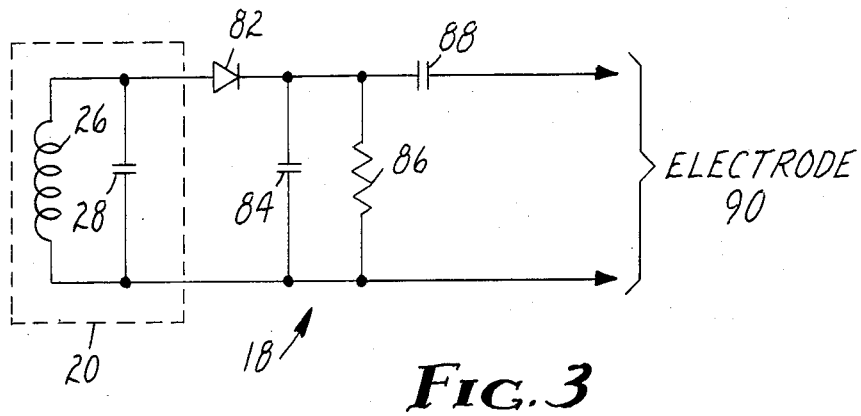
FIG. 3 is a schematic diagram of the receiver and the receiving antenna.

FIG. 3 represents a schematic diagram of receiver 18 and receiving antenna 20. Again, as in FIG. 1, receiving antenna 20 consists of inductor 26 parallel coupled to capacitor 28. Of course, various other tank circuits are envisioned for this receiving antenna 20. Receiving antenna 20 drives diode 82, capacitor 84 with resistor 86, which together with DC blocking capacitor 88 demodulate the signal for transmission to an electrode or other load for the transmitted signal. In a preferred embodiment, the load is an electrode which is implanted in the ear as an auditory hearing prosthesis to stimulate body tissue and, in particular, the auditory nerve.

Table 1 illustrates examples of values for the components utilized in the transmitter described in FIG. 2 and the receiver described in FIG. 3.

TABLE I

| Reference Numeral | Component | Value | Vendor |
| --- | --- | --- | --- |
| 22 | Inductor | 400 nanohenries | |
| 24 | Capacitor | 310 picofarads | |
| 26 | Inductor | 1.76 microhenries | |
| 28 | Capacitor | 100 picofarads | |
| 38 | Resistor | 16 kilohms | |
| 40 | Resistor | 4 kilohms | |
| 42 | Resistor | 1.6 megohms | |
| 44 | Operational Amplifier | CA 3420 | RCA |
| 46 | Transistor | MPS-C6595 | Motorola |
| 48 | Resistor | 10 ohms | |
| 50 | Transistor | MPS-C6595 | Motorola |
| 52 | Transistor | MPS-C6595 | |
| 54 | Resistor | 2.2 kilohms | |
| 56 | Resistor | 2.2 kilohms | |
| 58 | Resistor | 33 kilohms | |
| 60 | Resistor | 10 kilohms | |
| 62 | Resistor | 24 kilohms | |
| 64 | Resistor | 2.2 kilohms | |
| 66 | Resistor | 2.2 kilohms | |
| 68 | Transistor | MPS-C6595 | Motorola |
| 70 | Capacitor | 0.01 microfarads | |
| 72 | Capacitor | 0.01 microfarads | |
| 76 | Capacitor | 0.1 microfarads | |
| 82 | Diode | 1N5711 | |
| 84 | Capacitor | 1,000 picofarads | |
| 86 | Resistor | 3.3 kilohms | |
| 88 | Capacitor | 0.1 microfarads | |

Figure 4:
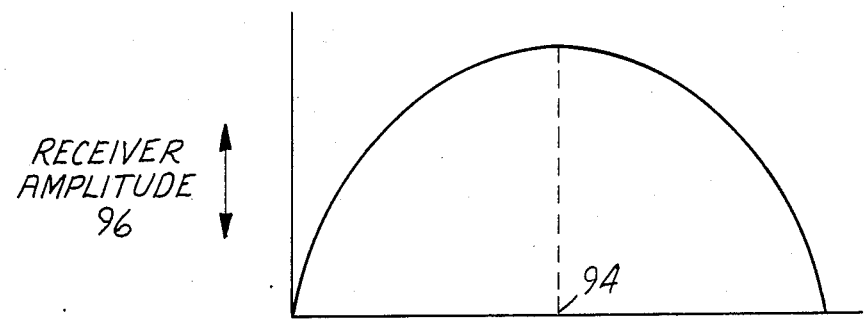
FIG. 4 is a graph illustrating prior art variations in receiving level versus antenna spacing.

FIG. 4 is a graph in which the spacing between the antenna coils of the transmitting antenna 14 and the receiving antenna 20 is plotted against the amplitude of the voltage of the received signal at the receiver 18. As can be seen in the graph, there is a spacing 94 between the coils of the transmitting antenna 14 and the receiving antenna 20 at which the amplitude of the voltage of the received signal is at a maximum. Also note that the slope of the curve is at a minimum at that particular spacing. It is at this spacing between the coils of the transmitting antenna 14 and the receiving antenna 20 that variations in the antenna spacing provide a minimal effect on the voltage amplitude of the received signal. Thus, the point 94 illustrated in FIG. 4 is the point of "critical coupling" between the transmitting antenna 14 and the receiving antenna 20.

Figure 5:
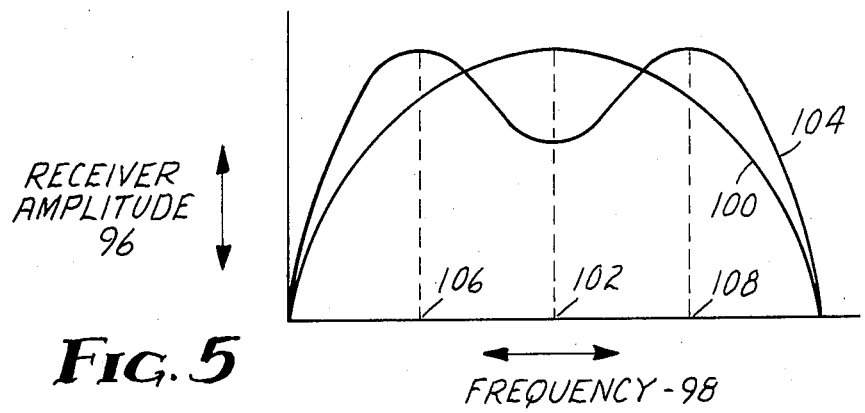
FIG. 5 is a graph illustrating the level of amplitude of received signal as a function of frequency.

FIG. 5 illustrates a graph in which the amplitude of the received signal 96 is plotted against the frequency 98 of operation of the transmitter oscillator. When the coils of the transmitting antenna 14 and the receiving antenna 20 are critically aligned and spaced and when the resonant frequencies of the transmitting antenna 14 and the receiving antenna 20 are identical, line 100 on the graph illustrates the effect of variations in the frequency of operation of the signal transmission system upon the amplitude of the received signal 96. From the graph it can be seen that there is a preferred frequency of operation 102 at which the amplitude of the received signal 96 is at a maximum and which variations in the frequency 98 of operation of the signal transmission system will result in minimal changes in the received amplitude 96 due to the minimum of slope of the curve 100. However, as the coils of the transmitting antenna 14 and the receiving antenna 20 are spaced at closer than the critical coupling distance or if the resonant frequencies are not identical, the curve in FIG. 5 differs. An example of the curve representing the received amplitude 96 as a function of the frequency 98 of operation is shown by curve 104. Instead of a single peak at frequency 102, the curve 104 demonstrates that there are really two amplitude peaks occurring on either side of frequency of 102. Note that the receiving amplitude 96 at the maximum in curve 104 is virtually identical to the received amplitude 96 of curve 100. That amplitude, however, is achieved at a different frequency of oscillation. Thus, the preferred frequency of oscillation for curve 104 differs from the frequency of operation for curve 100. With the transmitter 12 and receiver 18 of the present invention coupled with the transmitting antenna 14 and receiving antenna 20, the frequency of oscillation of the oscillator of transmitter 12 will automatically track to either frequency 100 or 108 maintaining the virtually identical received amplitude 96, albeit at a different frequency.

Thus, the unique transmitter 12, transmitting antenna 14 positioned in conjunction with receiving antenna 20 and receiver 18 provide a unique signal transmission system in which the received amplitude 96 of the signal at the receiver 18 is relatively independent of variations in coil misalignment between the transmitting antenna 14 and receiving antenna 20 as well as mismatches between the resonant frequencies of the transmitting antenna 14 and the receiving antenna 20. This is because the frequency of oscillation of the oscillator of transmitter 12 will automatically track to the proper frequency due to the resonant load which that oscillator drives.

Thus, it has been seen that there has been shown and described a novel signal transmission system. It is to be recognized and understood, however, that various changes, modifications and substitutions in the form and details of the present invention can be made by those skilled in the art without departing from the scope of the following claims.

What is claimed is:

1. A signal transmission system for use in transmitting a signal across a barrier, comprising:
    a radio frequency receiver for use on one side of said barrier;
    a receiving resonant antenna for use on said one side of said barrier being operatively coupled to said radio frequency receiver, said receiving resonant antenna having a resonant frequency;
    a transmitting resonant antenna for use on the opposite side of said barrier nearby said receiving resonant antenna, said transmitting resonant antenna having a resonant frequency;
    said resonant frequency of said receiving resonant antenna being relatively close to said resonant frequency of said transmitting resonant antenna;
    a radio frequency transmitter for use on said opposite side of said barrier being operatively coupled to said transmitting resonant antenna, said radio frequency transmitter having an oscillator having a frequency of oscillation driving a resonant load where said resonant load includes said transmitting resonant antenna inductively coupled with said receiving resonant antenna, said frequency of oscillation of said oscillator tracking to the resonant frequency of said resonant load maintaining a virtually identical amplitude of a received signal in said signal transmission system;
    whereby said signal transmission system is relatively independent of the distance between said transmitting resonant antenna and of said receiving resonant antenna, of radial misalignment between said transmitting resonant antenna and said receiving resonant antenna, and resonant frequency mismatch of said transmitting resonant antenna and said receiving resonant antenna.

2. A signal transmission system as in claim 1 wherein said resonant frequency of said receiving resonant antenna is within ten percent of said resonant frequency of said transmitting resonant antenna.

3. A signal transmission system as in claim 1 in which said receiving resonant antenna and said transmitting resonant antenna are positioned with respect to each other for critical coupling.

4. A signal transmission system as in claim 1 wherein said transmitting resonant antenna comprises a parallel coupled inductor and capacitor combination.

5. A signal transmission system as in claim 4 wherein said transmitter has only one resonant circuit.

6. A signal transmission system for use in a transcutaneous environment, comprising:
    a radio frequency receiver for subcutaneous use;
    a receiving resonant antenna for subcutaneous use being operatively coupled to said radio frequency receiver, said receiving resonant antenna having a resonant frequency;
    a transmitting resonant antenna for supercutaneous use nearby said receiving resonant antenna, said transmitting resonant antenna having a resonant frequency;
    said resonant frequency of said receiving resonant antenna being relatively close to said resonant frequency of said transmitting resonant antenna;
    a radio frequency transmitter for supercutaneous use being operatively coupled to said transmitting resonant antenna, said radio frequency transmitter having an oscillator having a frequency of oscillation driving a resonant load whereby said resonant load includes said transmitting resonant antenna inductively coupled with said receiving resonant antenna, said frequency of oscillation of said oscillator tracking to the resonant frequency of said resonant load maintaining a virtually identical amplitude of a received signal in said signal transmission system;
    whereby said signal transmission system is relatively independent of the distance between said transmitting resonant antenna and said receiving resonant antenna, of radial misalignment between said transmitting resonant antenna and said receiving resonant antenna, and resonant frequency mismatch of said transmitting resonant antenna and said receiving resonant antenna.

7. A signal transmission system as in claim 6 wherein said resonant frequency of said receiving resonant antenna is within ten percent of said resonant frequency of said transmitting resonant antenna.

8. A signal transmission system as in claim 6 wherein said transmitting resonant antenna comprises a parallel coupled inductor and capacitor combination.

9. A signal transmission system as in claim 8 wherein said transmitter has only one resonant circuit.

10. A signal transmission system for use in transmitting a signal across a barrier, comprising:
 a radio frequency receiver for use on one side of said barrier;
 a receiving resonant antenna for use on said one side of said barrier being operatively coupled to said radio frequency receiver, said receiving resonant antenna having a resonant frequency;
 a transmitting resonant antenna for use on the opposite side of said barrier nearby said receiving resonant antenna, said transmitting resonant antenna having a resonant frequency and comprising a parallel coupled inductor and capacitor combination;
 said resonant frequency of said receiving resonant antenna being relatively close to said resonant frequency of said transmitting resonant antenna;
 a radio frequency transmitter for use on said opposite side of said barrier being operatively coupled to said transmitting resonant antenna, said radio frequency transmitter having an oscillator having a frequency of oscillation driving a resonant load where said resonant load includes said transmitting resonant antenna inductively coupled with said receiving resonant antenna, said frequency of oscillation of said oscillator being at least partially determined by the resonant frequency of said resonant load, said radio frequency transmitter having a pair of transistors which are alternately active at a rate which is a function of the resonant frequency of said transmitting resonant antenna as influenced by said receiving resonant circuit.

11. A signal transmission system for use in a transcutaneous environment, comprising:
 a radio frequency receiver for subcutaneous use;
 a receiving resonant antenna for subcutaneous use being operatively coupled to said radio frequency receiver, said receiving resonant antenna having a resonant frequency;
 a transmitting resonant antenna for supercutaneous use nearby said receiving resonant antenna, said transmitting resonant antenna having a resonant frequency and comprising a parallel coupled inductor and capacitor combination;
 said resonant frequency of said receiving resonant antenna being relatively close to said resonant frequency of said transmitting resonant antenna;
 a radio frequency transmitter for supercutaneous use being operatively coupled to said transmitting resonant antenna, said radio frequency transmitter having an oscillator having a frequency of oscillation driving a resonant load whereby said resonant load includes said transmitting resonant antenna inductively coupled with said receiving resonant antenna, said frequency of oscillation of said oscillator being at least partially determined by the resonant frequency of said resonant load, said radio frequency transmitter having a pair of transistors which are alternately active at a rate which is a function of the resonant frequency of said transmitting resonant antenna as influenced by said receiving resonant antenna.

* * * * *